(12) United States Patent
Ohashi et al.

(10) Patent No.: US 8,168,779 B2
(45) Date of Patent: *May 1, 2012

(54) ANHYDROUS CRYSTALLINE β-MALTOSE, ITS PREPARATION AND USES

(75) Inventors: Tetsuya Ohashi, Okayama (JP); Hajime Aga, Okayama (JP); Tetsuya Nakada, Okayama (JP); Toshio Miyake, Okayama (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 542 days.

This patent is subject to a terminal disclaimer.

(21) Appl. No.: 12/307,671

(22) PCT Filed: Jul. 5, 2007

(86) PCT No.: PCT/JP2007/063477
§ 371 (c)(1),
(2), (4) Date: Jan. 6, 2009

(87) PCT Pub. No.: WO2008/004626
PCT Pub. Date: Jan. 10, 2008

(65) Prior Publication Data
US 2009/0292116 A1    Nov. 26, 2009

(30) Foreign Application Priority Data
Jul. 6, 2006 (JP) ................................ 2006-186309

(51) Int. Cl.
*C13K 7/00* (2006.01)
(52) U.S. Cl. ................................. 536/123.13
(58) Field of Classification Search ........................ None
See application file for complete search history.

(56) References Cited

U.S. PATENT DOCUMENTS

| 4,803,077 A | 2/1989 | Mitsuhashi et al. |
| 4,816,445 A | 3/1989 | Mitsuhashi et al. |
| 4,870,059 A | 9/1989 | Mitsuhashi et al. |
| 4,996,196 A | 2/1991 | Mitsuhashi et al. |

FOREIGN PATENT DOCUMENTS

| EP | 0252760 A | 1/1988 |
| EP | 1995332 A | 11/2008 |
| JP | 60-92299 A | 5/1985 |
| JP | 62-136240 A | 6/1987 |
| JP | 5-43360 B2 | 7/1993 |
| JP | 5-59697 B2 | 8/1993 |
| JP | 06-277100 A | 10/1994 |
| WO | 2007/074763 A1 | 7/2007 |

OTHER PUBLICATIONS

Thompson, A. et al., Journal of the American Chemical Society, "Acid Reversion Products from D-Glucose", 1954, vol. 76, No. 5, pp. 1309-1311.*
Anonymous,"Octaacetyl-beta-maltose," Chemblink, online database of chemicals from around the world, 2007, pp. 1-1, URL:http://web.archive.org/web/20070327181656/http://www.chemblink.com/products/22352-19-8.htm>.
J Hodge, et al., "Useful properties of maltose", Cereal Science Today, Jul. 1972, p. 180-188, vol. 17, American Association of Cereal Chemists, Inc., St. Paul, Minnesota.

* cited by examiner

*Primary Examiner* — Shaojia Anna Jiang
*Assistant Examiner* — Bahar Schmidtmann
(74) *Attorney, Agent, or Firm* — Browdy and Neimark, PLLC

(57) ABSTRACT

Objects of the present invention are to provide a novel anhydrous crystalline β-maltose, its preparation and uses. The present invention attains the above objects by providing an anhydrous crystalline β-maltose with a melting point of 154 to 159° C.; a process for producing the same, comprising a step of keeping hydrous crystalline β-maltose in an organic solvent at an ambient temperature or higher for the dehydration; and uses of the same.

4 Claims, 9 Drawing Sheets

ANHYDROUS CRYSTALLINE β-MALTOSE, ITS PREPARATION AND USES

TECHNICAL FIELD

The present invention relates to an anhydrous crystalline β-maltose, its preparation and uses, particularly, to a novel anhydrous crystalline β-maltose with a melting point of 154 to 159° C., a process for producing the same, comprising a step of keeping hydrous crystalline β-maltose in an organic solvent at an ambient temperature or higher for the dehydration, and uses of the same as a base for solidifying or powderizing moisture-containing or alcohol-containing compositions.

BACKGROUND ART

Maltose is a reducing disaccharide where two glucose molecules are bound together via the α-1,4 linkage, and is called as "malt sugar". Since maltose has a reducing end, i.e., an aldehyde group, α-anomer (α-maltose) and β-anomer (β-maltose) are present as isomers. It is known that monohydrous crystal (hereinafter, simply called as "hydrous crystal") and anhydrous crystal are present as crystalline maltose. Hydrous crystalline maltose is usually obtained as β-maltose, and a powdery product comprising hydrous crystalline β-maltose is produced on an industrial scale and commercialized.

While, an anhydrous crystalline maltose can be obtained from a concentrated solution with a moisture content of less than 5% (w/w) (Ref. Japanese Patent Kokoku No. 43,360/93). Since the anhydrous crystalline maltose contains 55 to 80% (w/w) of α-anomer and 20 to 45% (w/w) of β-anomer, the entity is α/β complex crystal. However, since the anhydrous crystalline maltose has a relatively high α-anomer content, it is usually called "anhydrous crystalline α-maltose" (Ref. Japanese Patent Kokoku Nos. 43,360/93 and 10,341/95). Since the anhydrous crystalline α-maltose absorbs moisture and is converted into stable hydrous crystalline β-maltose, and the resulting hydrous crystalline β-maltose does not absorb moisture under conditions of a relative humidity of 90% or lower, the anhydrous crystalline α-maltose is applied for powderizing foods containing moisture (Ref. Japanese Patent Kokoku Nos. 59,697/93 and 10,341/95). The above anhydrous crystalline α-maltose is commercialized by Hayashibara Shoji Inc., Okayama, Japan, as "FINETOSE®".

Japanese Patent Kokoku No. 59,697/93 and J. E. Hodge et al., "Cereal Science Today", Vol. 17, 7, pp. 180-188 (1972) disclose an anhydrous crystalline β-maltose and a method for preparing the anhydrous crystalline β-maltose by heating hydrous crystalline β-maltose under a reduced pressure for dehydration. However, since the anhydrous crystalline β-maltose has a defect of easily absorbing moisture, it has not been produced on an industrial scale yet. In the above literature by J. E. Hodge et al., it is reported that the anhydrous crystalline β-maltose, obtained by the above method, shows a melting point of 120 to 125° C. However, an anhydrous crystalline β-maltose with a melting point higher than 125° C. has been hitherto unknown.

DISCLOSURE OF THE INVENTION

An object of the present invention is to provide a novel anhydrous crystalline maltose, its preparation and uses.

The present inventors have extensively studied on a process for producing crystalline saccharides. In the course of their studies, it was unexpectedly found that an anhydrous crystalline maltose, obtained by keeping hydrous crystalline β-maltose in an organic solvent at an ambient temperature or higher for the dehydration, is a novel anhydrous crystalline β-maltose having a melting point of 154 to 159° C., which is lower than that (168 to 175° C.) of conventional anhydrous crystalline α-maltose (α/β complex anhydrous crystalline maltose) and higher than that (120 to 125° C.) of conventional anhydrous crystalline β-maltose disclosed in J. E. Hodge et al., "Cereal Science Today", Vol. 17, 7, pp. 180-188 (1972). It was also found that the novel anhydrous crystalline β-maltose has advantageous effects of having a relatively low moisture-absorbing property than well-known anhydrous crystalline β-maltose and being easily handled as a powdery crystal.

Further, it was unexpectedly found that the novel anhydrous crystalline β-maltose is more useful than well-known anhydrous crystalline α-maltose as a base for solidifying or powderizing moisture-containing or alcohol-containing compositions. Based on the above knowledge, the present inventors accomplished the present invention by establishing the novel anhydrous crystalline β-maltose, its preparation and uses.

The present invention attains the above objects by providing a novel anhydrous crystalline β-maltose having a melting point of 154 to 159° C., a process for producing the same, comprising a step of keeping hydrous crystalline β-maltose in an organic solvent at an ambient temperature or higher for the dehydration, and its uses as a base for solidifying or powderizing moisture-containing or alcohol-containing compositions.

Since the anhydrous crystalline β-maltose of the present invention shows an advantageous property of having a relatively lower moisture-absorbing property than conventional anhydrous crystalline β-maltose, it can be easily handled as a powdery crystal. According to the present invention, the novel anhydrous crystalline β-maltose can be easily produced by the process comprising a step of dehydrating hydrous crystalline maltose in an organic solvent. When the anhydrous crystalline β-maltose of the present invention is dissolved in water to give a relatively high concentration, hydrous crystalline β-maltose is quickly crystallized in the solution because the anomer of the material maltose is β-form. By using the crystallization, a moisture-containing composition can be solidified. When the powder of the anhydrous crystalline β-maltose of the present invention is allowed to absorb moisture, it is quickly converted into stable hydrous crystalline β-maltose while keeping the powdery form. Further, since the powder of the anhydrous crystalline β-maltose of the present invention has a porous structure and a relatively large intrusion volume, it can be used for retaining a relatively large amount of volatile substances such as alcohols. Based on the above properties, the anhydrous crystalline β-maltose of the present invention can be more advantageously used as a base for solidifying or powderizing moisture-containing or alcohol-containing compositions for various foods and beverages, cosmetics, and pharmaceuticals than conventional anhydrous crystalline α-maltose which has been used in the art.

EXPLANATION OF SYMBOLS

Figure 9:
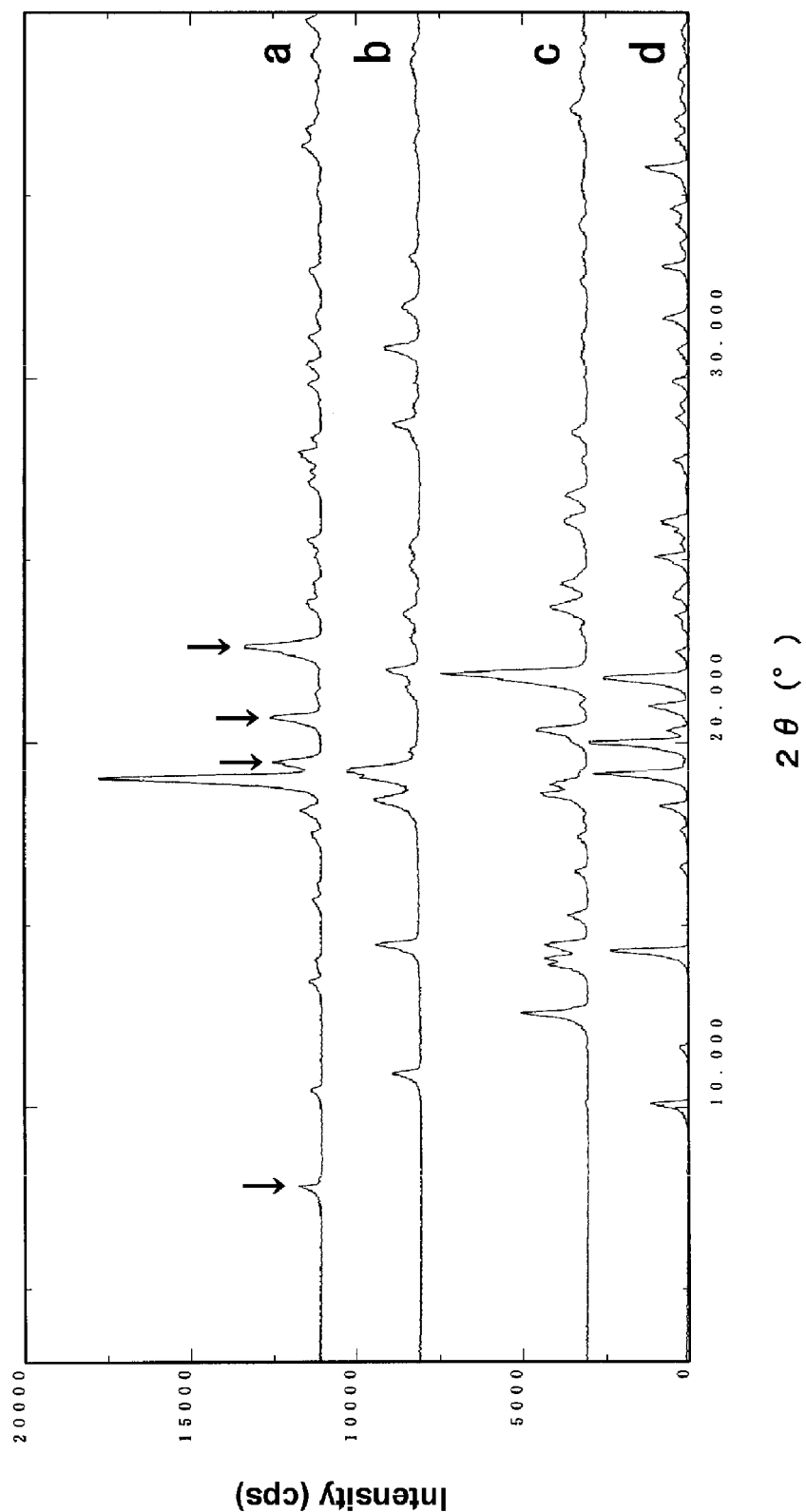
FIG. 9 shows powdery X-ray diffraction diagrams of an anhydrous crystalline maltose converted by the ethanol treatment and those of the hydrous crystalline β-maltose of Control 1, anhydrous crystalline α-maltose of Control 2, and anhydrous crystalline β-maltose of Control 3.

In FIG. 9,
a: Anhydrous crystalline maltose converted by the ethanol treatment (Present Invention)
b: Anhydrous crystalline β-maltose (Control 3)
c: Anhydrous crystalline α-maltose (Control 2)
d: Hydrous crystalline maltose (Control 1)
↓: Characteristic diffraction peaks of the anhydrous crystalline maltose converted by the ethanol treatment In FIG. 10,
a: Anhydrous crystalline maltose converted by the ethanol treatment (Present Invention)
b: Anhydrous crystalline β-maltose (Control 3)
c: Anhydrous crystalline α-maltose (Control 2)

Figure 11:
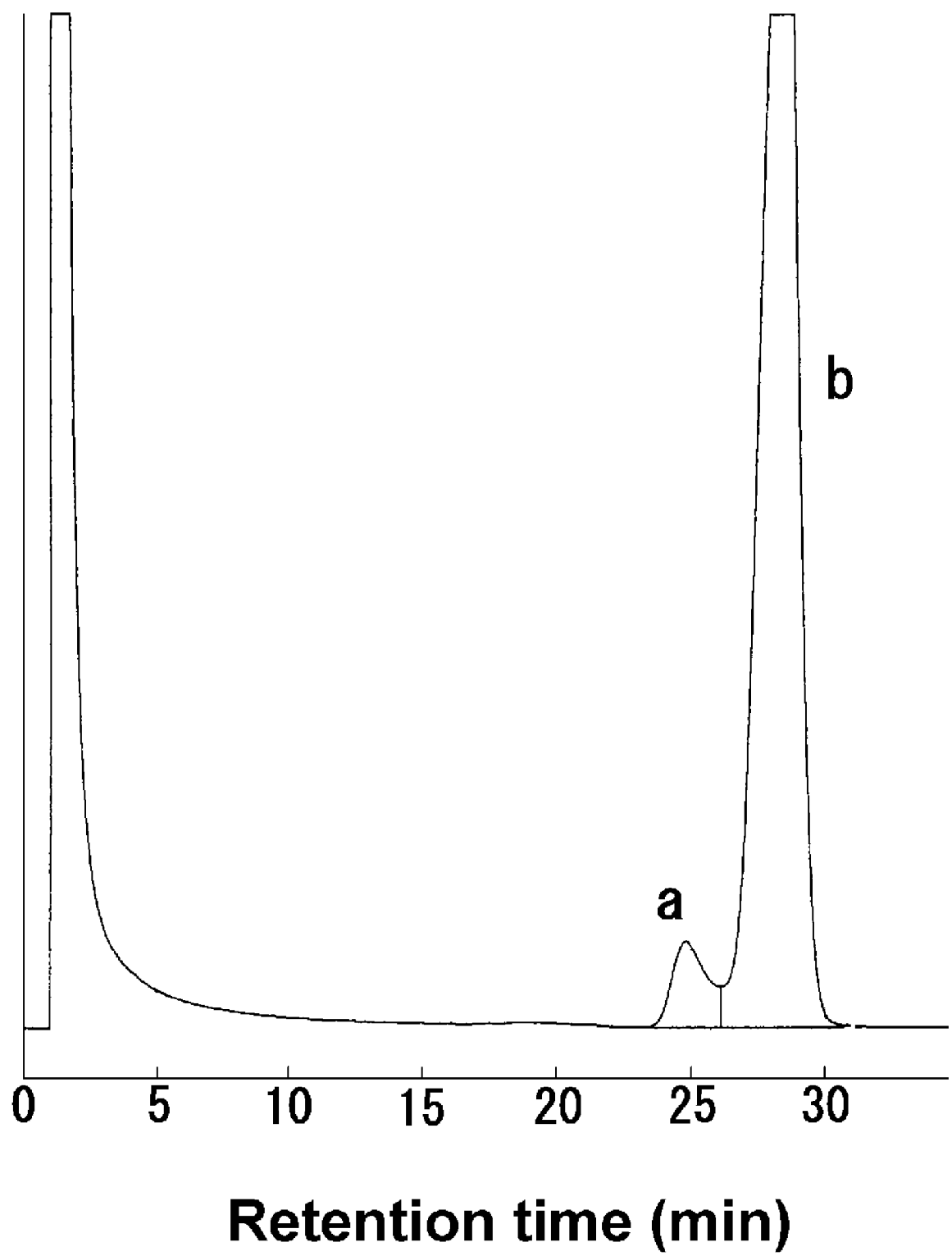
FIG. 11 shows a GLC chromatogram for measuring an α/β anomer ratio of an anhydrous crystalline maltose converted by the ethanol treatment.

In FIG. 11,
a: α-Anomer of maltose (α-maltose)
b: β-Anomer of maltose (β-maltose)

Figure 12:
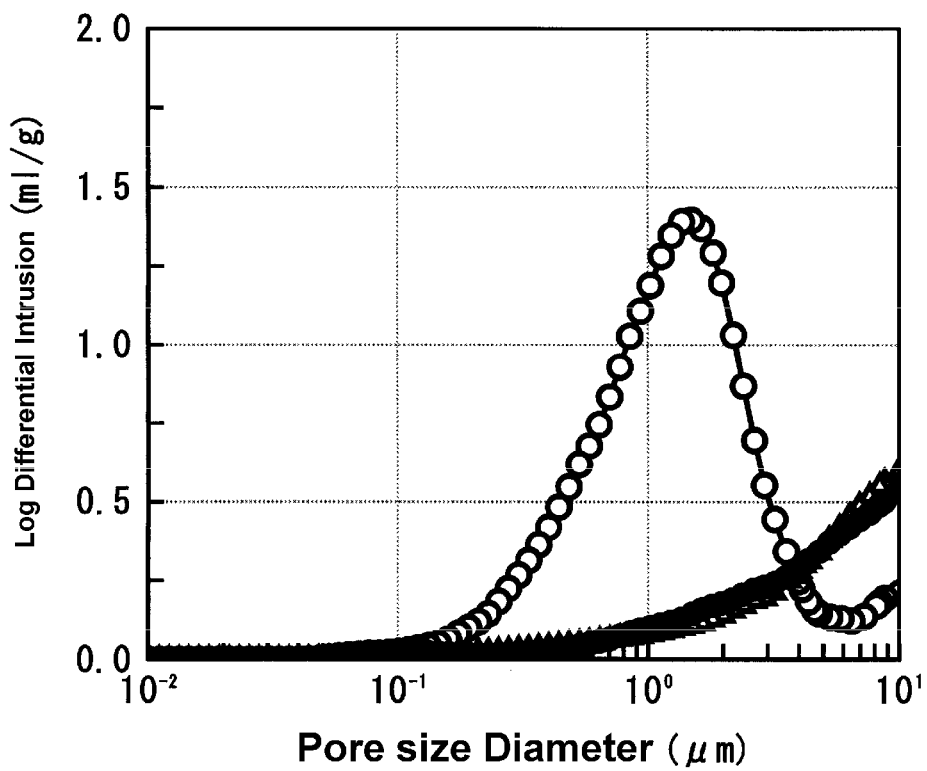
FIG. 12 shows pore size distributions of an anhydrous crystalline β-maltose converted by the ethanol treatment, measured by the mercury filling method, and those of the anhydrous crystalline α-maltose of Control 2 and anhydrous crystalline β-maltose of Control 3.

In FIG. 12,
○: Anhydrous crystalline maltose converted by the ethanol treatment (Present Invention)
●: Anhydrous crystalline β-maltose (Control 3)
∆: Anhydrous crystalline α-maltose (Control 2)

Figure 13:
FIG. 13 shows a photograph showing the results of a deionized water-solidifying test (after 2 hours from the dissolution of samples) comparing the usefulness of an anhydrous crystalline β-maltose converted by the ethanol treatment (Present invention) and the anhydrous crystalline α-maltose (Control) as a base for the solidification.
Figure 14:
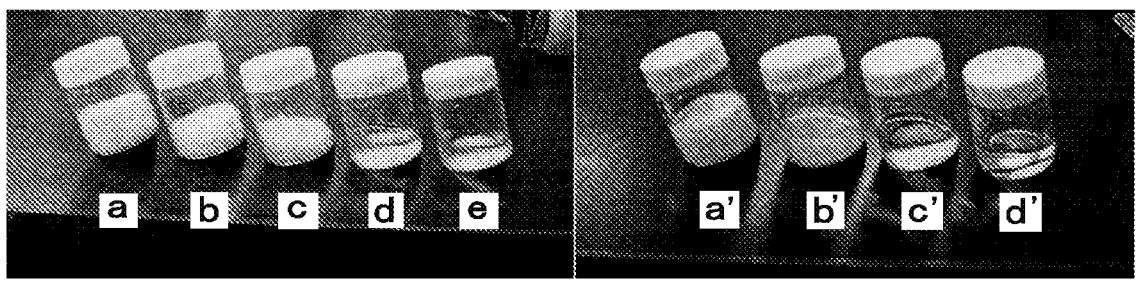
FIG. 14 shows a photograph showing the results of a deionized water-solidifying test (after 20 hours from the dissolution of samples) comparing the usefulness of an anhydrous crystalline β-maltose converted by the ethanol treatment (Present invention) and the anhydrous crystalline α-maltose (Control) as a base for the solidification.

In FIGS. 13 and 14,
a to e: Samples prepared by dissolving 18.8, 13.3, 11.5, 10.0 or 8.2 g of an anhydrous crystalline β-maltose converted by the ethanol treatment (Present invention)
a' to d': Samples prepared by dissolving 18.8, 13.3, 11.5, or 10.0 g of the anhydrous crystalline α-maltose (Control)

Figure 15:
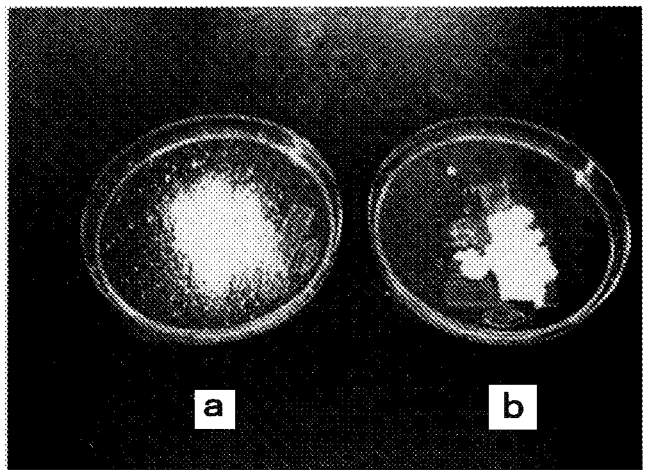
FIG. 15 shows a photograph showing the results of a deionized water-admixing test comparing the usefulness of an anhydrous crystalline β-maltose converted by the ethanol treatment (Present invention) and the anhydrous crystalline α-maltose (Control) as a base for the powderization.

In FIG. 15,
a: Sample prepared by admixing 1.25 ml of deionized water with 10 g of an anhydrous crystalline β-maltose converted by the ethanol treatment (Present invention)
b: Sample prepared by admixing 1.25 ml of deionized water with 10 g of the anhydrous crystalline α-maltose (Control)

Figure 16:
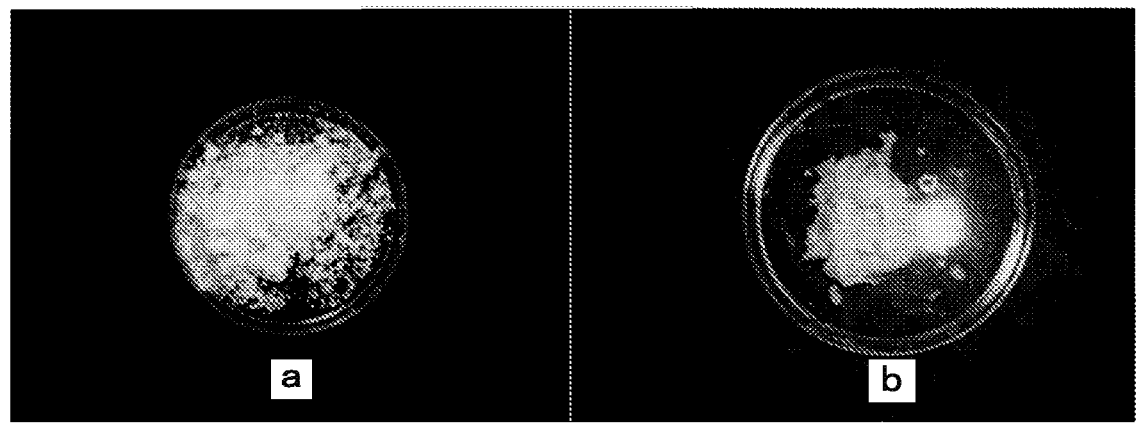
FIG. 16 shows a photograph showing the results of an ethanol-admixing test comparing the usefulness of an anhydrous crystalline β-maltose converted by the ethanol treatment (Present invention) and the anhydrous crystalline α-maltose (Control) as a base for the powderization.

In FIG. 16,
a: Sample prepared by admixing 6 ml of ethanol with 10 g of an anhydrous crystalline β-maltose converted by the ethanol treatment (Present invention)
b: Sample prepared by admixing 6 ml of ethanol with 10 g of the anhydrous crystalline α-maltose (Control)

BEST MODE FOR CARRYING OUT THE INVENTION

The anhydrous crystalline β-maltose of the present invention is a novel anhydrous crystalline β-maltose having a melting point of 154 to 159° C. The anhydrous crystalline β-maltose of the present invention usually contains 90% or higher of β-anomer (β-maltose) as an isomer of maltose. Further, the anhydrous crystalline β-maltose of the present invention shows characteristic peaks on a powdery X-ray diffraction diagram at diffraction angles (2θ) of 7.8°, 19.5°, 20.7°, and 22.6°, which are not detected in conventional hydrous crystalline β-maltose, anhydrous crystalline α-maltose, and anhydrous crystalline β-maltose.

The anhydrous crystalline β-maltose of the present invention may have a form of porous crystal having a number of fine pores. The term "porous crystal" as referred to as in the present invention means specifically a crystalline saccharide showing a number of fine pores when photographed with a scale factor of, for example, 2,000-folds using a scanning electron microscope (hereinafter, abbreviated as "SEM"). The porous crystal has a relatively large specific surface area and specific pore size distribution as physical properties. Specifically, the porous crystal of the anhydrous crystalline β-maltose of the present invention has unique physical properties as follows:

(a) a specific surface area is 1 $m^2/g$ or higher when determined by a gas adsorption isotherms using nitrogen (hereinafter, called as "nitrogen adsorption isotherms"); and (b) an intrusion volume of pores is 0.1 ml/g or higher and the pores show a clear peak in a range of a pore size diameter of lower than 5 μm, when a pore size distribution is measured by a mercury filling method.

The anhydrous crystalline β-maltose of the present invention can be produced by dehydrating hydrous crystalline β-maltose in an organic solvent at an ambient temperature or higher. As an organic solvent, it is preferable to use, usually, an organic solvent with a relatively high polarity and being easily blended in water such as alcohols and acetone, desirably, an alcohol aqueous solution with an alcohol content of 85% or higher, more desirably, an ethanol aqueous solution with an ethanol content of 85% or higher.

When hydrous crystalline β-maltose is dehydrated, a ratio of the hydrous crystalline β-maltose and an organic solvent is not restricted as far as the object can be attained. In the case of using ethanol as the organic solvent, a preferable volume of ethanol to the weight of hydrous crystalline β-maltose is, usually, 5-folds or higher, desirably, 10-folds or higher. Considering a time required for the treatment, it is preferable to control a temperature for the dehydration, usually, at 40° C. or higher, desirably, 50° C. or higher, more desirably, 60° C. or higher. In the dehydration, it is preferable to stir the organic solvent suspended with hydrous crystalline β-maltose for the efficient dehydration. After the dehydration, the organic solvent used for the dehydration contains water, but the solvent is reusable after distillation.

Conventional anhydrous crystalline β-maltose easily absorbs moisture and can be hardly handled as a powdery crystal, while the anhydrous crystalline β-maltose of the present invention has advantageous characteristics that it shows a relatively low hygroscopicity and can be easily handled. The anhydrous crystalline β-maltose of the present invention is converted into hydrous crystalline β-maltose as in the cases of conventional anhydrous crystalline β-maltose and anhydrous crystalline α-maltose when it is allowed to absorb moisture under a relatively high humidity condition, but it shows no excess absorption of moisture different from conventional anhydrous crystalline maltose. Further, since a porous crystal of the anhydrous crystalline β-maltose of the present invention has a number of pores and a relatively large specific surface area, it shows advantageous solubility in water in comparison with conventional hydrous crystalline β-maltose, particularly, can be dissolved rapidly into cold water.

When the anhydrous crystalline β-maltose of the present invention is allowed to dissolve into water to give a relatively high concentration, i.e., a concentration higher than the saturation concentration of hydrous crystalline β-maltose, the crystal is dissolved in water and then hydrous crystalline β-maltose is quickly crystallized from the resulting solution and solidified into a block. As described later in Examples, in the case of investigating conventional anhydrous crystalline α-maltose which has been used for powderizing moisture-containing compositions, it requires a relatively high concentration and a relatively long time for the crystallization and solidification of hydrous crystalline β-maltose. While, the anhydrous crystalline β-maltose of the present invention can be used for quickly crystallizing and solidifying hydrous crystalline β-maltose even at a relatively low concentration. The characteristic of the anhydrous crystalline β-maltose of the present invention can be used for solidifying various moisture-containing compositions, for example, alcoholic liquors such as "sake", juices such as fruits juice and vegetable juice, syrups, and lipid- and moisture-containing compositions such as whipping cream, into a block form. Therefore, the anhydrous crystalline β-maltose of the present invention is useful in the various fields such as food industry.

When the anhydrous crystalline β-maltose of the present invention is allowed to absorb moisture, it is quickly converted into hydrous crystalline β-maltose with keeping its powdery form. Therefore, using the anhydrous crystalline β-maltose of the present invention, a powdery juice can be prepared easily. Further, since the porous anhydrous crystalline β-maltose of the present invention has a number of pores, a relatively large specific surface area, and a large intrusion volume, it has a characteristic of retaining a relatively large amount of alcohols or lipids with keeping its powdery form. Using the characteristic, powdery alcohols and powdery lipids can be prepared easily.

The porous anhydrous crystalline β-maltose of the present invention can be applied for various uses by using the physical properties, i.e., a number of pores, large specific surface area, and large intrusion volume. For example, various useful materials can be stabilized by enclosing useful materials in pores of the porous crystal. Also, the porous crystal can be used as a microcapsule by enclosing volatile fragrances in the pores and sealing the pores by coating. Further, since the porous crystal contains air in the pores, it has a whipping property and can be used for preparing fine whipped creams. Rightfully, the porous anhydrous crystalline β-maltose of the present invention can be used in the fields of foods and beverages, cosmetics, medicated cosmetics, and pharmaceuticals as in well-known hydrous crystalline β-maltose and anhydrous crystalline α-maltose.

The following examples explain the present invention in detail. However, the present invention should not be restricted thereby.

Example 1

Preparation of an Anhydrous Crystalline Maltose

In a 2-L round bottom flask equipped with a stirrer and a thermometer, 1,200 ml of ethanol was placed and preheated at 70° C. Then, 120 g of "MALTOSE OM", a maltose product with a purity of 98% or higher, produced by Hayashibara Co., Ltd., Okayama, Japan, was admixed with the preheated ethanol and stirred at 170 rpm. At constant intervals, about 100 ml each of the crystal suspension was collected and centrifuged to separate solid and liquid using a basket-type centrifugal separator, and the ethanol adhered to crystal surface was removed by spreading the collected crystal onto a palette and drying the resultant in a circulation dryer at 50° C. for 20 min. The moisture content of the resulting crystal was measured by conventional Karl Fischer's method. The time course of the moisture content of the crystal is shown in Table 1.

TABLE 1

| Time (min) | Crystal moisture content (%, w/w) |
|---|---|
| 0 | 5.24 |
| 40 | 5.51 |
| 55 | 5.28 |
| 90 | 5.43 |
| 130 | 5.30 |
| 160 | 5.38 |
| 180 | 5.01 |
| 210 | 4.34 |
| 240 | 3.68 |
| 270 | 2.85 |
| 330 | 1.38 |
| 480 | 0.32 |

As is evident from Table 1, it was revealed that a moisture content of the hydrous crystalline β-maltose is decreased to less than 1% (w/w) by the dehydration in ethanol (ethanol conversion) at 70° C. for 480 min and hydrous crystalline β-maltose is converted into anhydrous crystalline maltose. The moisture content and crystallinity, determined by Ruland method based on a powdery X-ray diffraction diagram, of the anhydrous crystalline maltose preparation, obtained by treating for 480 min, were 0.32% (w/w) and 78%, respectively. Hereinafter, the anhydrous crystalline maltose, obtained by heating and dehydrating in ethanol, is called as "the anhydrous crystalline maltose converted by the ethanol treatment" in distinction to conventional anhydrous crystalline maltose.

Example 2

Physical Properties of the Anhydrous Crystalline Maltose Converted by the Ethanol Treatment The following maltose preparations, (i), (ii), and (iii), were used as Control 1, Control 2, and Control 3, respectively, for comparing the physical properties with those of the anhydrous crystalline maltose converted by the ethanol treatment:
(i) Hydrous crystalline β-maltose, used as a material in Example 1;
(ii) Conventional anhydrous crystalline α-maltose (produced by Hayashibara Co., Ltd., Okayama, Japan, α/β complex crystal, maltose content of 98% or higher); and
(iii) Anhydrous crystalline β-maltose, prepared by heating hydrous crystalline β-maltose at 95° C. for 40 hours under a reduced pressure according to the method disclosed in J. E. Hodge et al., "*Cereal Science Today*", Vol. 17, 7, pp. 180-188 (1972).

Moisture contents, ratios of α- and β-anomer (hereinafter, called "anomer ratio") determined by gas-liquid chromatography (GLC), and crystallinities determined by Ruland method based on their powdery X-ray diffraction diagrams, of crystalline maltose preparations, Controls 1 to 3, are summarized in Table 2.

TABLE 2

| Crystalline maltose | | Moisture content (%, w/w) | Anomer ratio (α:β) | Crystallinity (%) |
|---|---|---|---|---|
| Control 1 | Hydrous crystalline β-maltose | 5.24 | 4:96 | 83 |
| Control 2 | Anhydrous crystalline α-maltose | 0.74 | 71:29 | 74 |
| Control 3 | Anhydrous crystalline β-maltose | 0.24 | 12:88 | 64 |

Example 2-1

Figure 1:
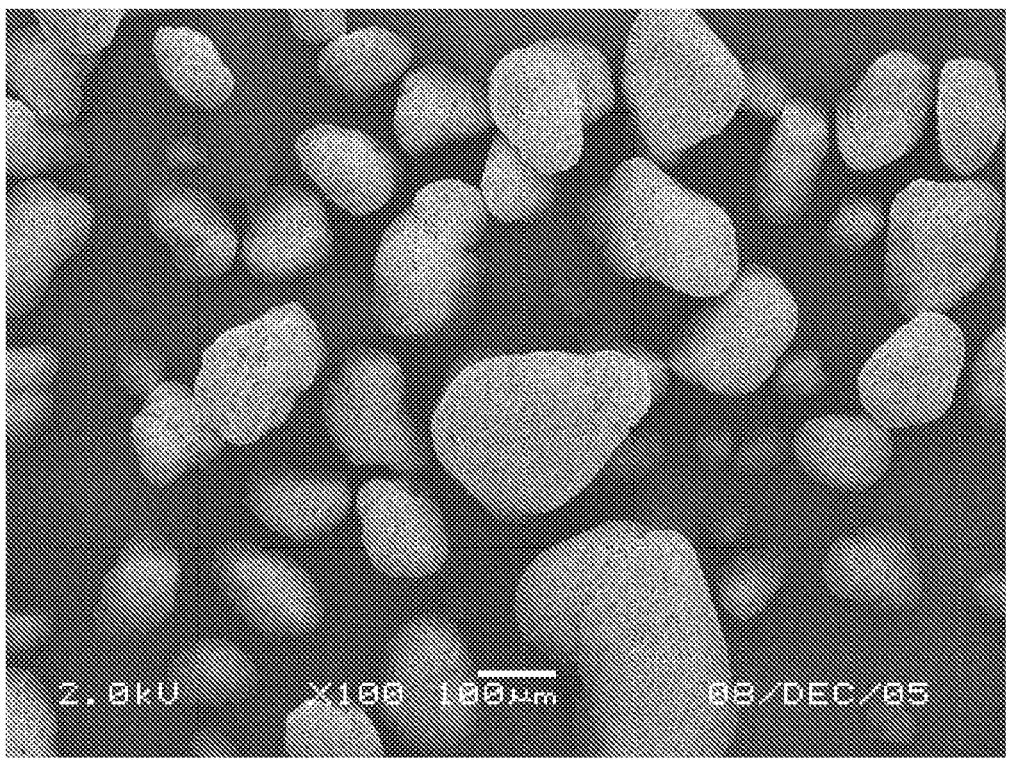
FIG. 1 shows a SEM photograph (×100) of an anhydrous crystalline maltose obtained by treating in ethanol at 70° C. for 480 min.
Figure 2:
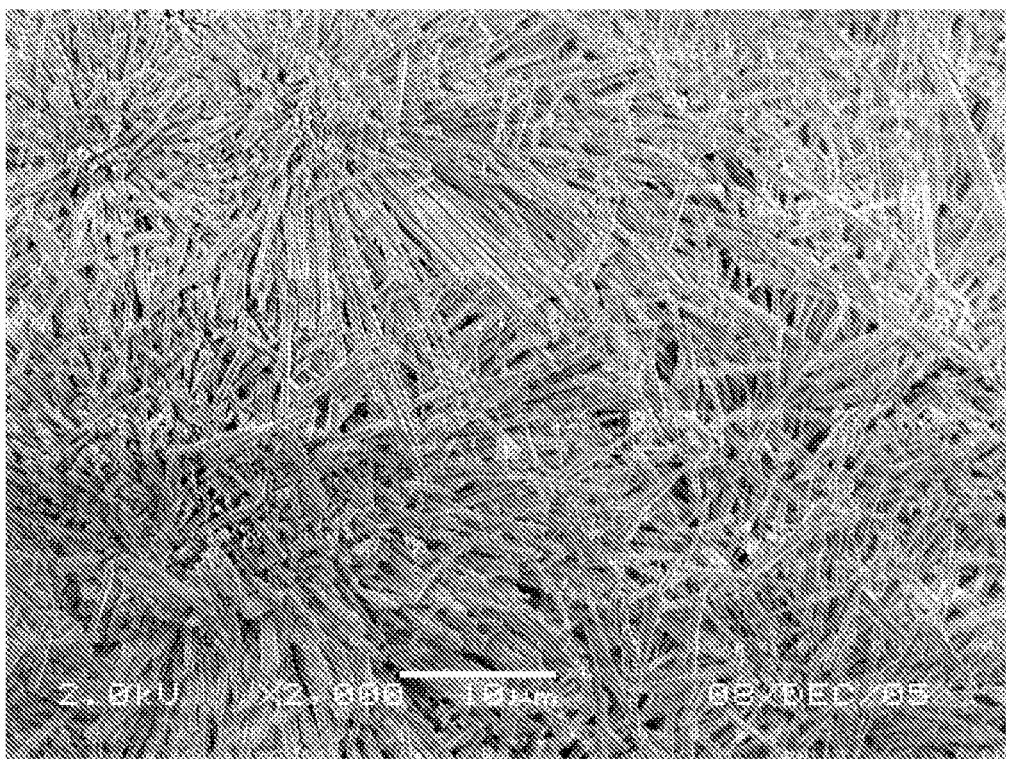
FIG. 2 shows a SEM photograph (×2,000) of an anhydrous crystalline maltose obtained by treating in ethanol at 70° C. for 480 min.
Figure 3:
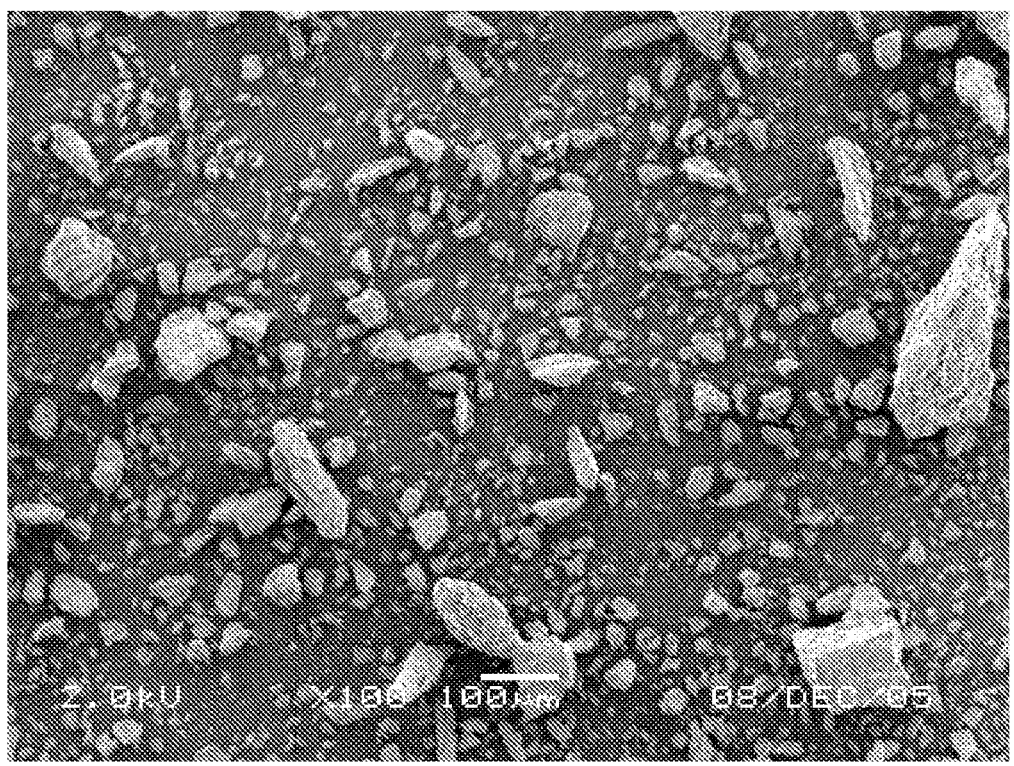
FIG. 3 shows a SEM photograph (×100) of the hydrous crystalline maltose of Control 1.
Figure 5:
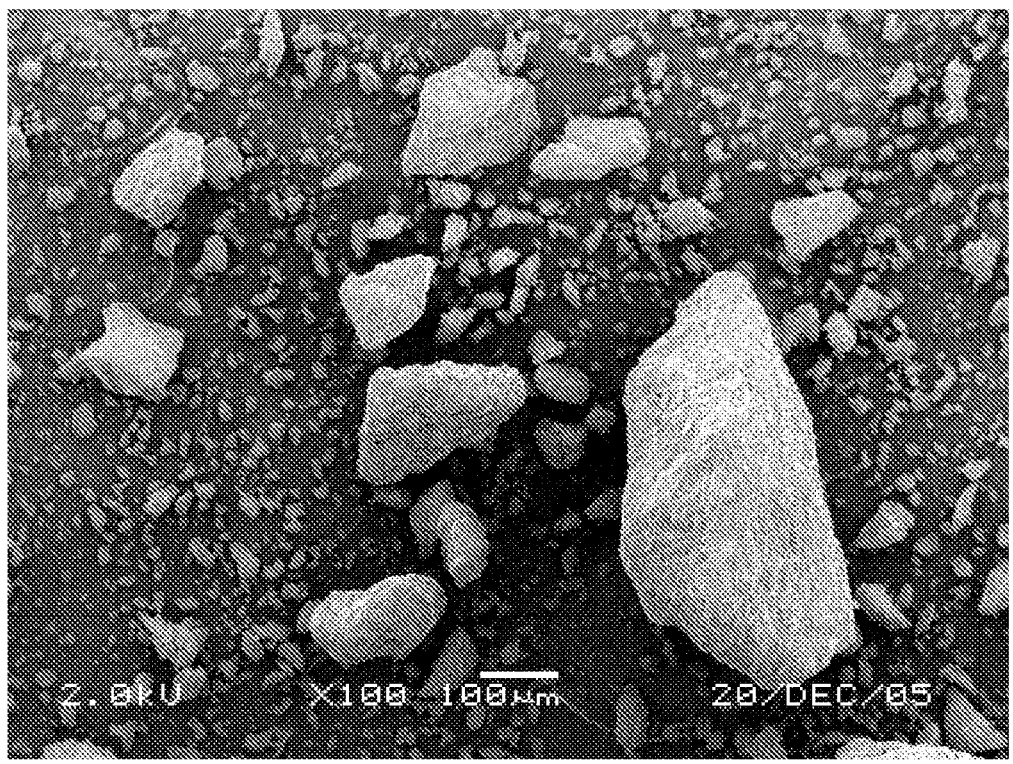
FIG. 5 shows the SEM photograph (×100) of the anhydrous crystalline α-maltose of Control 2.
Figure 7:
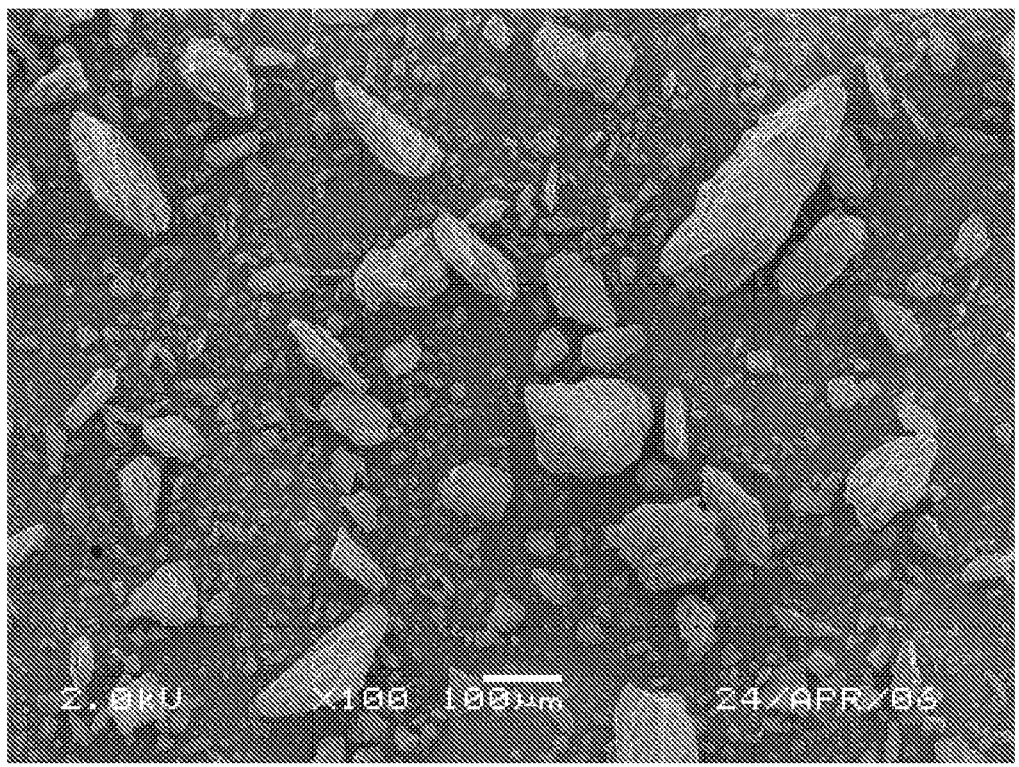
FIG. 7 shows a SEM photograph (×100) of the anhydrous crystalline β-maltose of Control 3.

SEM Photograph of the Anhydrous Crystalline Maltose Converted by the Ethanol Treatment SEM photographs of the anhydrous crystalline maltose converted by the ethanol treatment in Example 1, are shown in FIG. 1 (×100) and FIG. 2 (×2,000). Similarly, SEM photographs of crystalline maltose of Control 1, Control 2, and Control 3 are shown in FIGS. 3 (×100) and 4 (×2,000), and FIGS. 5 (×100) and 6 (×2,000), and FIGS. 7 (×100) and 8 (×2,000), respectively.

Figure 4:
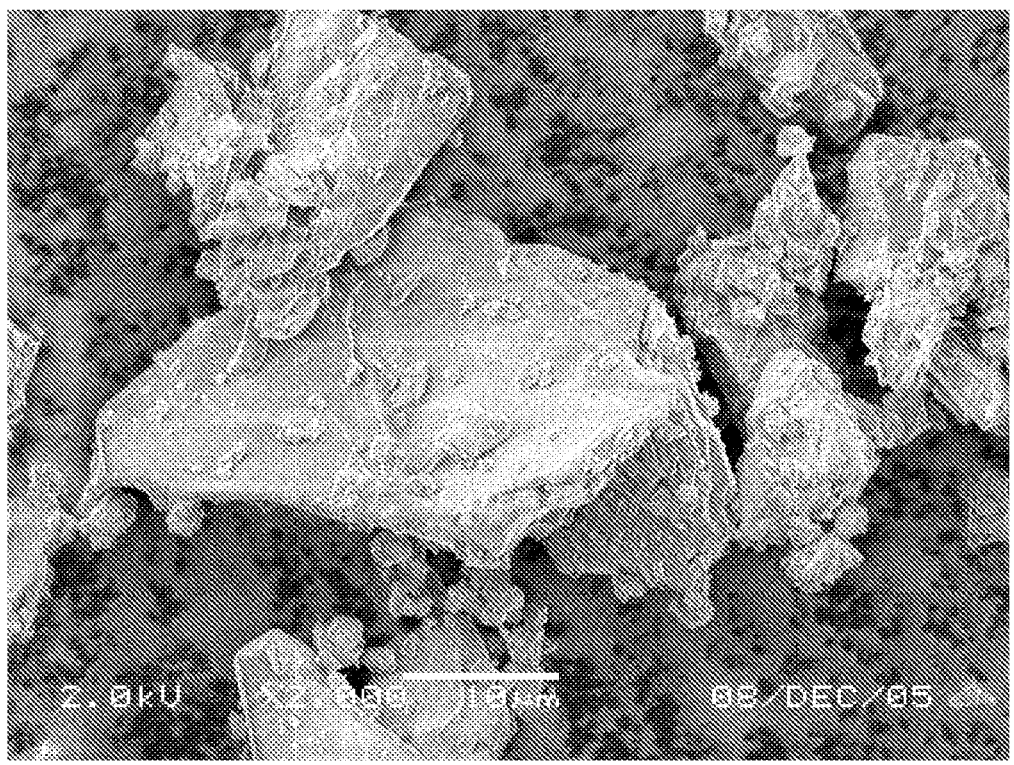
FIG. 4 shows a SEM photograph (×2,000) of the hydrous crystalline maltose of Control 1.
Figure 6:
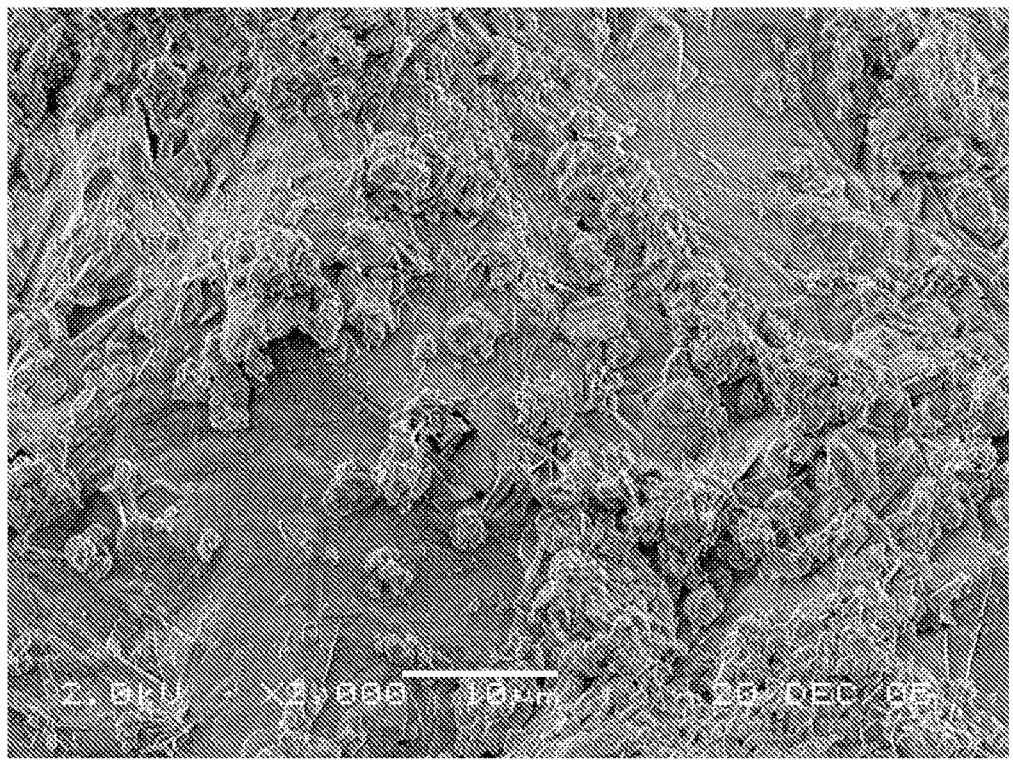
FIG. 6 shows a SEM photograph (×2,000) of the anhydrous crystalline α-maltose of Control 2.
Figure 8:
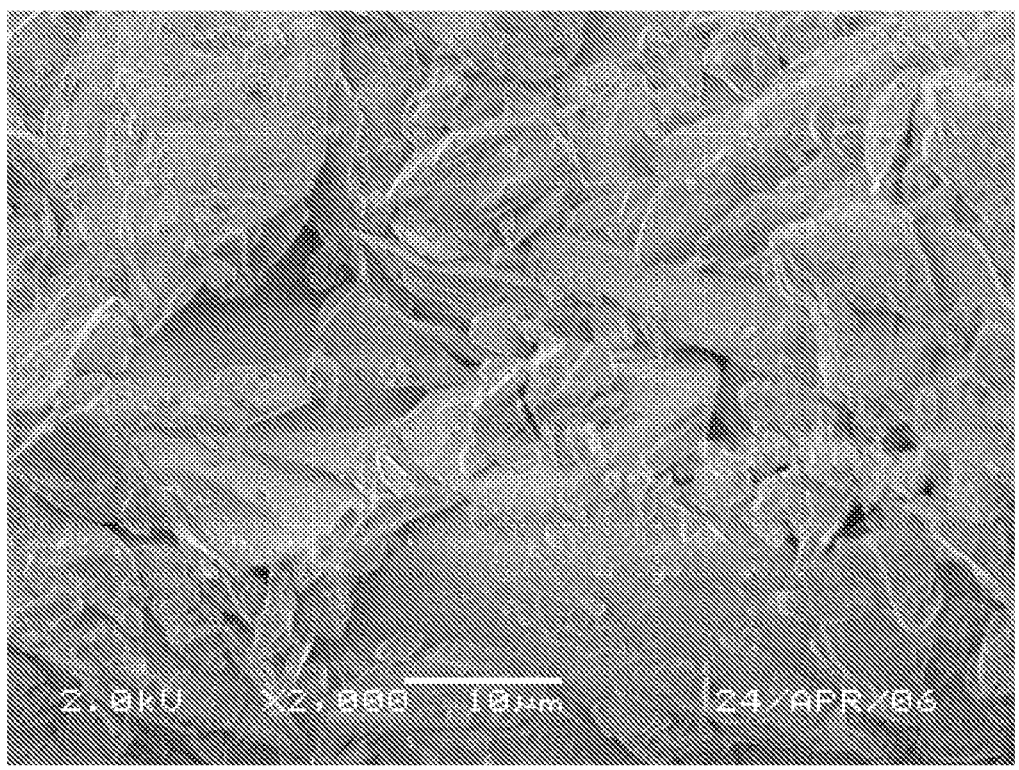
FIG. 8 shows a SEM photograph (×2,000) of the anhydrous crystalline β-maltose of Control 3.

As is evident from FIGS. 4, 6, and 8, pores were hardly observed in material hydrous crystalline β-maltose (Control 1), anhydrous crystalline α-maltose prepared by conventional method (Control 2), and anhydrous crystalline β-maltose prepared according to the method disclosed in the literature by J. E. Hodge et al (Control 3). While, as shown in FIG. 2, an anhydrous crystalline maltose obtained by heating and dehydrating in ethanol showed an aggregate of fine columnar crystals and a number of pores, revealing that the anhydrous crystalline maltose has a porous structure.

Example 2-2

Powdery X-Ray Diffraction Diagram of the Anhydrous Crystalline Maltose Converted by the Ethanol Treatment Powdery X-ray diffractometry of the anhydrous crystalline maltose converted by the ethanol treatment was carried out using Cu—Kα radiation and "GEIGERFLEX RDA-IIB", a powdery X-ray diffractometer commercialized by Rigaku Co., Tokyo, Japan. The powdery X-ray diffraction diagram of the anhydrous crystalline maltose converted by the ethanol treatment in Example 1 and those of crystalline maltose preparations, Controls 1 to 3, are shown in FIG. 9.

As is evident from FIG. 9, the powdery X-ray diffraction diagram of the anhydrous crystalline maltose converted by the ethanol treatment (FIG. 9, Symbol "a") was completely different from those of an anhydrous crystalline β-maltose of Control 3 (FIG. 9, Symbol "b"), an anhydrous crystalline α-maltose of Control 2 (FIG. 9, Symbol "c"), and a hydrous crystalline β-maltose of Control 1 (FIG. 9, Symbol "d"). The anhydrous crystalline maltose converted by the ethanol treatment showed characteristic peaks on a powdery X-ray diffraction diagram at diffraction angles (2θ) of 7.8°, 19.5°, 20.7°, and 22.6°, which are not detected in the crystalline maltoses of Controls 1 to 3. The results indicate that the anhydrous crystalline maltose converted by the ethanol treatment has a crystal form completely different from those of well-known crystalline maltose.

Example 2-3

Differential Scanning Calorimetry of the Anhydrous Crystalline Maltose Converted by the Ethanol Treatment An endothermic pattern on differential scanning calorimetry (DSC) of samples was measured using "DSC8230", a differential scanning calorimeter commercialized by Rigaku Co., Tokyo, Japan. The endothermic pattern of the anhydrous crystalline maltose, converted by the ethanol treatment in Example 1, and those of the anhydrous crystalline maltoses of Control 2 and Control 3 are shown in FIG. 10.

Figure 10:
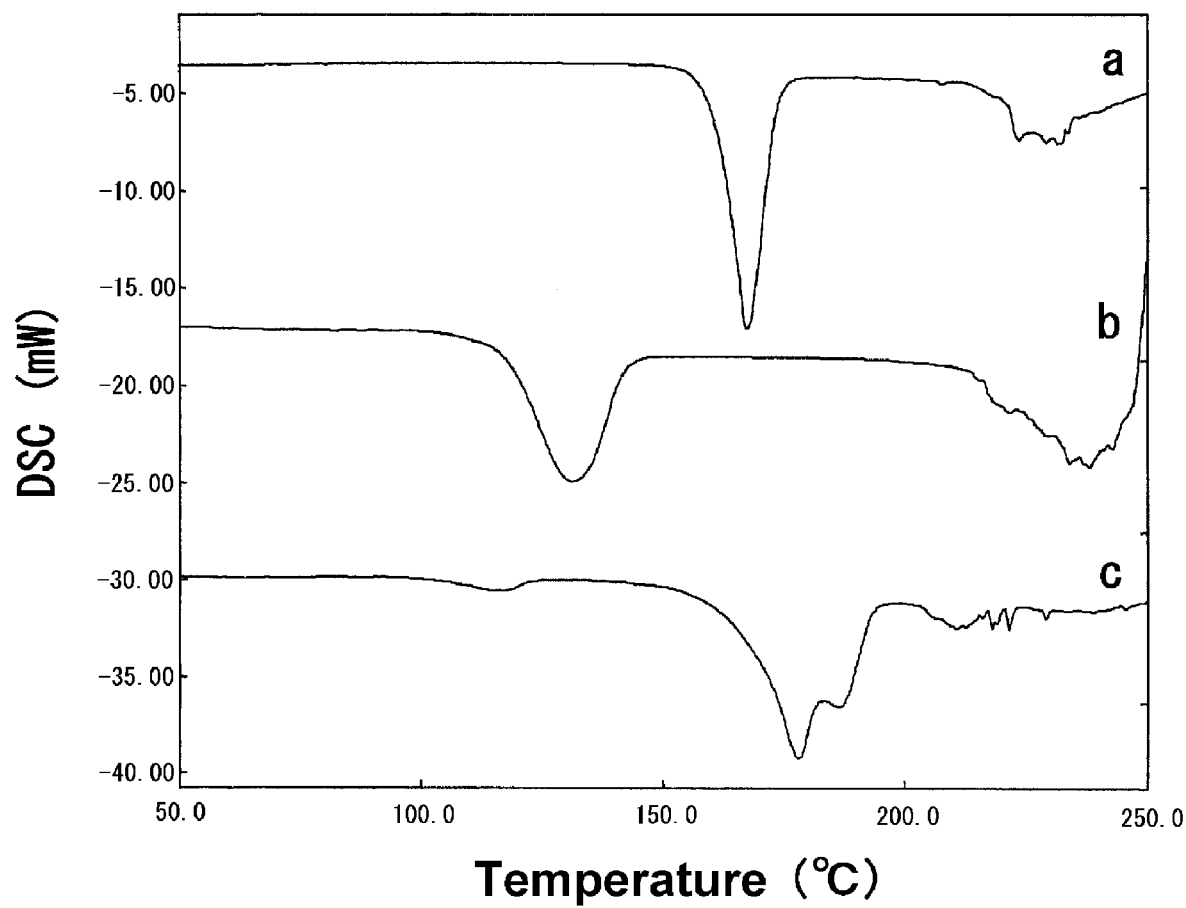
FIG. 10 shows endothermic patterns on differential scanning calorimetry (DSC) of an anhydrous crystalline maltose converted by the ethanol treatment and those of the anhydrous crystalline α-maltose of Control 2 and anhydrous crystalline β-maltose of Control 3.

As is evident from FIG. 10, an endothermic pattern of the anhydrous crystalline maltose converted by the ethanol treatment (FIG. 10, Symbol "a") showed a sharp endothermic peak at 167.3° C. While, that of the anhydrous crystalline β-maltose of Control 3 (FIG. 10, Symbol "b") showed an endothermic peak at 131.4° C., and that of the anhydrous crystalline α-maltose of Control 2 (FIG. 10, Symbol "c") showed broad endothermic peaks at 176.8° C. and 187.7° C. The endothermic pattern of the anhydrous crystalline maltose converted by the ethanol treatment was completely different from those of the anhydrous crystalline maltoses of Control 2 and Control 3.

Based on the facts that a powdery X-ray diffraction diagram and an endothermic pattern on DSC analysis of the anhydrous crystalline maltose converted by the ethanol treatment were completely different from those of the conventional well-known anhydrous crystalline maltoses used as Control 2 and Control 3, the anhydrous crystalline maltose converted by the ethanol treatment in Example 1 is concluded to be a novel anhydrous crystalline maltose. Successively, a melting point and an anomer ratio of the anhydrous crystalline maltose converted by the ethanol treatment were measured and the results were compared with those of the conventional anhydrous crystalline maltoses of Control 2 and Control 3 in the following Examples 2-4 and 2-5.

Example 2-4

Melting Point of the Anhydrous Crystalline Maltose Converted by the Ethanol Treatment The melting point of the anhydrous crystalline maltose converted by the ethanol treatment in Example 1 was measured by conventional method using "MP-21", a melting-point apparatus commercialized by Yamato Scientific Co., Ltd., Tokyo, Japan. As a result, it was revealed that the melting point of the anhydrous crystalline maltose converted by the ethanol treatment is 154 to 159° C. The value was clearly lower than 168 to 175° C., the melting point of well-known anhydrous crystalline α-maltose (α/β complex crystal, α-anomer content of 73%) described in the literature by J. E. Hodge, and clearly higher than 120 to 125° C., the melting point of well-known anhydrous crystalline β-maltose (β-anomer content of 88%) described in the same literature. The anhydrous crystalline maltose converted by the ethanol treatment in Example 1 is completely different from the conventional well-known anhydrous crystalline α-maltose and anhydrous crystalline β-maltose. The anhydrous crystalline maltose having a melting point of 154 to 159° C. is a novel anhydrous crystalline maltose which has been hitherto unknown.

Example 2-5

Anomer Ratio of the Anhydrous Crystalline Maltose Converted by the Ethanol Treatment About 70 mg of an anhydrous crystalline maltose, converted by the ethanol treatment in Example 1, was dissolved in 5 ml of anhydrous pyridine. Then, 100 μl of the resulting solution was used for conventional trimethylsilyl derivatization (TMS-derivatization) and the resulting sample was analyzed by gas-liquid chromatography (GLC) and the contents of α-anomer and β-anomer of maltose were calculated by the simple area percentage method to determine the anomer ratio. GLC was carried out under the following conditions:

<Conditions for GLC analysis>

Gas chromatograph: GC-14A, produced by Shimadzu Corporation, Kyoto, Japan;
Column: 2% Silicon OV-17/Chromosorb W/AW/DMCS column (ID 3 mm × 2 m);
Column temperature: 210° C.;
Temperature at the injector: 330° C.
Carrier gas: Nitrogen; Flow rate: 40 ml/min;
Combustion gas: Hydrogen; Flow rate: 40 ml/min;
Supporting gas: Air; Flow rate: 600 ml/min
Detector: FID A GLC chromatogram of the anhydrous crystalline maltose converted by the ethanol treatment is shown in FIG. 11. The α-anomer (FIG. 11, Symbol "a") and β-anomer (FIG. 11, Symbol "b") contents of the anhydrous crystalline maltose converted by the ethanol treatment in Example 1 were 5.5% and 94.5%, respectively, and the anhydrous crystalline maltose was made up of a majority of β-anomer. From the results in Example 2-5, it was revealed that the anhydrous crystalline maltose converted by the ethanol treatment is a β-maltose. Based on the result, the anhydrous crystalline maltose converted by the ethanol treatment is called as "the anhydrous crystalline β-maltose converted by the ethanol treatment", hereinafter.

Example 2-6

Specific Surface Area of the Anhydrous Crystalline β-Maltose Converted by the Ethanol Treatment The specific surface area of the anhydrous crystalline β-maltose converted by the ethanol treatment was measured by a nitrogen adsorption isotherms using "MODEL ASAP-2400", a specific surface area/pore size distribution analyzer commercialized by Micromeritics, Georgia, USA. About 3 g of the anhydrous crystalline β-maltose, obtained in Example 1, was dried in the apparatus under a reduced pressure at about 40° C. for about 15 hours as a pretreatment, and then used for the measurement of specific surface area by the nitrogen adsorption isotherms. The result was analyzed by conventional BET (Brunnauer, Emmet, and Teller) method. Those of the anhydrous crystalline α-maltose of Control 2 and the anhydrous crystalline β-maltose of Control 3 were measured by the same method.

The specific surface area of the anhydrous crystalline β-maltose converted by the ethanol treatment was determined to be 3.39 $m^2/g$, and those of the anhydrous crystalline α-maltose of Control 2 and anhydrous crystalline β-maltose of Control 3 were 0.48 $m^2/g$, and 0.82 $m^2/g$, respectively. The specific surface area of the anhydrous crystalline β-maltose converted by the ethanol treatment was about 7- to 4-folds larger than those of the controls. The anhydrous crystalline β-maltose converted by the ethanol treatment showed a relatively large specific surface area due to a number of pores.

Example 2-7

Pore Size Distribution of the Anhydrous Crystalline β-Maltose Converted by the Ethanol Treatment The pore size distribution and intrusion volume of the anhydrous crystalline β-maltose converted by the ethanol treatment were measured by a mercury filling method using "AUTOPORE 9520", a pore size distribution analyzer commercialized by Micromeritics, Georgia, USA. About 0.5 g of the anhydrous crystalline maltose, obtained by treating in ethanol at 70° C. for 480 min in Example 1, was sampled and the pore size distribution was measured using an initial pressure of 15 kPa. Those of the anhydrous crystalline α-maltose of Control 2 and the anhydrous crystalline β-maltose of Control 3 were also measured by the same method. The results are in Table 3, and the pore size distribution charts are in FIG. 12.

TABLE 3

| Sample | Intrusion volume (ml/g) | Median pore diameter (μm) | Mode pore diameter (μm) |
|---|---|---|---|
| Anhydrous crystalline β-maltose converted by the ethanol treatment (Present invention) | 1.05 | 1.26 | 1.44 |
| Anhydrous crystalline α-maltose (Control 2) | (No pore) | 13.00 | 20.70 |
| Anhydrous crystalline β-maltose (Control 3) | (No pore) | 14.70 | 25.70 |

As is evident from Table 3, the anhydrous crystalline β-maltose converted by the ethanol treatment showed a relatively large intrusion volume, i.e., 1.05 ml/g and a clear peak in the pore size diameter of less than 5 μm (FIG. 12, "○"). In FIG. 12, the pore size distributions, observed in the anhydrous crystalline α-maltose of Control 2 and the anhydrous crystalline β-maltose of Control 3 (FIG. 12, Symbols "Δ" and "●") were not originated from pores and originated from a phenomenon of injecting mercury to the space between crystal particles because of the small particle size.

Example 3

Hygroscopicity of the Anhydrous Crystalline β-Maltose Converted by the Ethanol Treatment Hygroscopicity of the anhydrous crystalline β-maltose converted by the ethanol treatment was compared with those of the hydrous crystalline β-maltose of Control 1, anhydrous crystalline α-maltose of Control 2, and anhydrous crystalline β-maltose of Control 3 by conventional hygroscopicity test. About one gram of either of the above crystalline maltose samples was precisely weighed out in an aluminum weighing cup (diameter: 50 mm×height: 25 mm), then the cups were placed in a closed container (300 mm×210 mm×100 mm) controlled to give a relative humidity (RH) of 47%, 58%, 75%, or 90% by using a saturated solution of lithium nitrate, sodium bromide, sodium chloride, or barium chloride, and kept at 27° C. for 2, 4, 6, 8, 24, 96, and 192 hours. Moisture contents of the samples at respective periods were measured based on the change of weight from the start of the test. The moisture contents of the samples at the start of the test were measured by Karl Fischer's method. The time courses of moisture contents of the samples at the respective humidity conditions are summarized in Table 4.

ture content of about 0.8% (w/w). The anhydrous crystalline β-maltose of Control 3 absorbed moisture from just after the start of the test under a humidity of RH 58%, to give a moisture content of about 7% (w/w) after four hours and then released moisture to give a moisture content of about 5.5% (w/w) after six to 24 hours from the start of the test. While, the anhydrous crystalline β-maltose converted by the ethanol treatment of the present invention kept a moisture content of about 0.4% (w/w) for 24 hours under a humidity of RH 58% and then absorbed moisture. The anhydrous crystalline β-maltose of the present invention showed a relatively low hygroscopicity in comparison with the conventional anhydrous crystalline β-maltose of Control 3.

As is also evident from the results in Table 4, under the condition of RH 90%, the anhydrous crystalline β-maltose of Control 3 and the anhydrous crystalline α-maltose of Control 2 absorbed moisture to give moisture contents of about 10% (w/w) and about 17% (w/w), respectively, which are higher than that of hydrous crystalline maltose, i.e., about 5.3%, and then released moisture. While, it was revealed that the anhydrous crystalline β-maltose converted by the ethanol treatment gradually absorbed moisture, with requiring 2 to 6 hours under the condition of RH 75% and zero to 4 hours under the condition of RH 90%, and was converted into hydrous crystalline maltose without showing an excess moisture content of over about 5.3% (w/w) as described above. The anhydrous crystalline β-maltose converted by the ethanol treatment of the present invention (a novel anhydrous crystalline β-maltose), having the above characteristic, is useful as a base for powderizing moisture-containing compositions without solidifying them.

TABLE 4

| Saturated solution of inorganic salt and RH | Sample | Moisture content of samples (%, w/w) Time (hour) | | | | | | | |
|---|---|---|---|---|---|---|---|---|---|
| | | 0 | 2 | 4 | 6 | 8 | 24 | 96 | 192 |
| Lithium nitrate RH 47% | AC* β-Mal (Present invention) | 0.32 | 0.30 | 0.28 | ND | ND | 0.27 | 0.34 | 0.28 |
| | AC β-Mal (Control 3) | 0.24 | 0.32 | 0.47 | ND | ND | 0.54 | 0.61 | 0.47 |
| | AC α-Mal (Control 2) | 0.74 | 0.70 | 0.70 | ND | ND | 0.65 | 0.71 | 0.70 |
| | HC** β-Mal (Control 1) | 5.24 | 5.23 | 5.23 | ND | ND | 5.23 | 5.26 | 5.23 |
| Sodium bromide RH 58% | AC β-Mal (Present invention) | 0.32 | 0.32 | 0.33 | 0.36 | 0.35 | 0.35 | 1.47 | 4.16 |
| | AC β-Mal (Control 3) | 0.24 | 4.68 | 6.92 | 6.71 | 6.28 | 5.63 | 5.48 | 5.42 |
| | AC α-Mal (Control 2) | 0.74 | 0.74 | 0.76 | 0.80 | 0.79 | 0.83 | 0.98 | 0.91 |
| | HC β-Mal (Control 1) | 5.24 | 5.22 | 5.25 | 5.26 | 5.25 | 5.25 | 5.28 | 5.26 |
| Sodium chloride RH 75% | AC β-Mal (Present invention) | 0.32 | 0.66 | 2.37 | 3.93 | 4.51 | 4.54 | 4.57 | 5.19 |
| | AC β-Mal (Control 3) | 0.24 | 6.86 | 6.76 | 6.47 | 6.34 | 6.16 | 6.01 | 5.93 |
| | AC α-Mal (Control 2) | 0.74 | 1.18 | 2.44 | 2.88 | 3.14 | 3.84 | 3.85 | 4.49 |
| | HC β-Mal (Control 1) | 5.24 | 5.21 | 5.25 | 5.25 | 5.25 | 5.25 | 5.29 | 5.23 |
| Barium chloride RH 90% | AC β-Mal (Present invention) | 0.32 | 1.72 | 4.53 | 4.79 | 4.58 | 4.66 | 4.82 | 5.38 |
| | AC β-Mal (Control 3) | 0.24 | 7.28 | 7.66 | 7.45 | 7.45 | 8.46 | 10.20 | 9.12 |
| | AC α-Mal (Control 2) | 0.74 | 1.79 | 4.30 | 6.29 | 7.82 | 15.78 | 17.77 | 14.38 |
| | HC β-Mal (Control 1) | 5.24 | 5.26 | 5.27 | 5.26 | 5.26 | 5.24 | 5.61 | 5.36 |

AC: Anhydrous crystal,
HC: Hydrous crystal
Mal: maltose,
ND: Not determined,
RH: Relative humidity As is evident from the results in Table 4, in the case of hydrous crystalline β-maltose of Control 1, the moisture content was hardly changed from about 5.3% (w/w) under all humidity conditions. It was revealed that the hydrous crystalline β-maltose of Control 1 is a stable crystal with low hygroscopicity. The anhydrous crystalline α-maltose of Control 2 absorbed moisture from just after the start of the test under humidity of RH 75% or higher, but it hardly absorbed moisture under humidity of RH 58% or lower and kept the mois- Example 4

Anhydrous Crystalline β-Maltose Converted by the Ethanol Treatment as a Base for Solidifying Aqueous Solution In order to investigate the usefulness of the anhydrous crystalline β-maltose converted by the ethanol treatment of the present invention as a base for solidifying moisture-containing compositions, a solidifying test was carried out using deionized water as a model of moisture-containing composition as follows. Ten grams of deionized water having a temperature of 25° C. was poured into a 60-ml glass vessel (Internal diameter: 44 mm, Height: 57 mm), and then, 8.2, 10.0, 11.5, 13.3, or 18.8 g of the anhydrous crystalline β-maltose converted by the ethanol treatment, obtained by the method in Example 1, was gradually admixed with the deionized water in one minute and dissolved with stirring at 240 to 250 rpm using a stirring bar. After completing the dissolution, each test solution was further stirred for four minutes and then the stirring was stopped. Successively, each test solution was left to stand and a solidification of the test solution by the crystallization of hydrous crystalline maltose was monitored macroscopically for two hours. In the cases of the solidified samples, the time of starting the crystallization and that of completing the solidification were checked. (However, the test solution dissolving 18.8 g of crystal was stopped stirring at three minutes after the dissolution because the crystallization of hydrous crystalline maltose was started immediately.) After monitoring macroscopically for two hours, each vessel containing any one of the sample solutions was closed and further left to stand for 18 hours. Then, the condition (appearance) of the test samples after 20 hours from the dissolution was monitored macroscopically and evaluated by the following three phases: (1) clear solution; (2) clouded solution; and (3) solidified. The samples prepared by using 10.0 g, 11.5 g, 13.3 g, or 18.8 g of the anhydrous crystalline α-maltose used in Example 2, as a substitute of the test samples, were treated by the same procedure as controls. The test was carried out in a room where a temperature was kept at 25° C. The results of each sample after 2 and 20 hours are shown in Table 5 and FIG. 13, and Table 6 and FIG. 14, respectively.

TABLE 5

| Amount of dissolved anhydrous crystalline maltose (g) | Conc.* (%) | Anhydrous crystalline β-maltose converted by the ethanol treatment (Present invention) | | Symbol in FIG. 13 | Anhydrous crystalline α-maltose (Control) | | Symbol in FIG. 13 |
|---|---|---|---|---|---|---|---|
| | | Time of solidification started (min) | Time of solidification completed (min) | | Time of solidification started (min) | Time of solidification Completed (min) | |
| 8.2 | 45.0 | Not solidified | Not solidified | e | ND** | ND** | ND** |
| 10.0 | 50.0 | Not solidified | Not solidified | d | Not solidified | Not solidified | d' |
| 11.5 | 53.5 | Not solidified | Not solidified | c | Not solidified | Not solidified | c' |
| 13.3 | 57.0 | 6.0 | 8.0 | b | Not solidified | Not solidified | b' |
| 18.8 | 65.0 | 3.0 | 3.5 | a | Not solidified | Not solidified | a' |

*Calculated concentration

**Not determined.

TABLE 6

| Amount of dissolved anhydrous crystalline maltose (g) | Conc.* (%) | Anhydrous crystalline β-maltose converted by the ethanol treatment (Present invention) Condition (Appearance) | Symbol in FIG. 14 | Anhydrous crystalline α-maltose (Control) Condition (Appearance) | Symbol in FIG. 14 |
|---|---|---|---|---|---|
| 8.2 | 45.0 | Not solidified (Clear solution) | e | ND** | ND** |
| 10.0 | 50.0 | Not solidified (Clear solution) | d | Not solidified (Clear solution) | d' |
| 11.5 | 53.5 | Not solidified (Clouded solution) | c | Not solidified (Clear solution) | c' |
| 13.3 | 57.0 | Solidified | b | Not solidified (Clouded solution) | b' |
| 18.8 | 65.0 | Solidified | a | Solidified | a' |

*Calculated concentration

**Not determined.

As is evident from Table 5 and FIG. 13, in the case of the test solution prepared by dissolving 18.8 g of the anhydrous crystalline β-maltose converted by the ethanol treatment, the crystallization was started at 3 min after the dissolution and the solidification was completed at 3.5 min after the dissolution (Symbol "a" in FIG. 13). In the case of the test solution prepared by dissolving 13.3 g of the anhydrous crystalline β-maltose converted by the ethanol treatment, the crystallization of hydrous crystalline maltose was started at 6 min after the dissolution and the solidification was completed at 8 min after the dissolution (Symbol "b" in FIG. 13). However, in the cases of test solutions prepared by dissolving 11.5 g or lower of the anhydrous crystalline β-maltose converted by the ethanol treatment (Symbols "c" to "e" in FIG. 13), the solidification was not observed. While, in the cases of the control solutions prepared by dissolving anhydrous crystalline α-maltose, the solidification during 2 hours after the dissolution was not observed in all control solutions (Symbols "a'" to "d'" in FIG. 13).

Also, as is evident from Table 6 and FIG. 14, in the cases of the test samples prepared by dissolving 18.8 g and 13.3 g of the anhydrous crystalline β-maltose converted by the ethanol treatment, which were solidified at 3.5 min and 8 min after the dissolution, the test samples kept their solidified phases even after 20 hours (Symbols "a" and "b" in FIG. 14). In the case of the test sample prepared by dissolving 11.5 g of the anhydrous crystalline β-maltose converted by the ethanol treatment, which was not solidified during 2 hours after the dissolution, partial crystallization of hydrous crystalline maltose was observed but the solidification was not observed even after 20 hours (Symbol "c" in FIG. 14). Also, in the cases of test samples prepared by dissolving 10.0 g or lower of the anhydrous crystalline β-maltose converted by the ethanol treatment (Symbols "d" and "e" in FIG. 14), crystallization was not observed. While, in the case of the control sample prepared by dissolving 18.8 g of the anhydrous crystalline α-maltose, the solidification was completed at 20 hours after the dissolution (Symbol "a'" in FIG. 14). However, in the case of the control sample prepared by dissolving 13.3 g, it was clouded solution (Symbol "b'" in FIG. 14). In the cases of the control samples prepared by dissolving 11.5 g or lower, the crystallization was not observed and the control samples kept the forms of clear solution (Symbols "c'" and "d'" in FIG. 14).

The above results indicate that the anhydrous crystalline β-maltose of the present invention can be used for solidifying moisture-containing compositions in lower amount and more quickly than anhydrous crystalline α-maltose, which has been used as a base for solidifying and powderizing moisture-containing compositions, and is useful as a base for the solidification.

Example 5

Solid Whiskey

Fifteen parts by weight of a commercially produced whiskey (40% proof) was put in a vessel, and then 20 parts by weight of the anhydrous crystalline β-maltose, converted by the ethanol treatment in Example 1, was gradually admixed with the whiskey with stirring. The admixed anhydrous crystalline β-maltose was completely dissolved in the whiskey, and after a brief interval, hydrous crystalline β-maltose was quickly crystallized from the whiskey solution and the whole content was solidified into a block form. The product is a solid whiskey with a smooth texture and fine sweetness and can be advantageously used for producing confectioneries.

Example 6

Solid Maple Syrup

A commercially produced maple syrup (saccharide concentration 66% (w/w)) was diluted with deionized water to give a saccharide concentration of 50% (w/w). Fourteen parts by weight of the diluted maple syrup was put in a vessel, and then nine parts by weight of the anhydrous crystalline β-maltose, converted by the ethanol treatment in Example 1, was gradually admixed with the syrup with stirring. The admixed anhydrous crystalline β-maltose was completely dissolved in the maple syrup, and after a brief interval, hydrous crystalline β-maltose was quickly crystallized from the syrup and the whole content was solidified into a block form. The product is a solid maple syrup with a smooth texture and can be advantageously used for producing confectioneries.

Example 7

Solid Whipping Cream

Fifteen parts by weight of a commercially produced whipping cream (amount of milkfat: 40% (w/w), a solid non fat: 4% (w/w)) was put in a vessel, and then 13.8 parts by weight of the anhydrous crystalline β-maltose, converted by the ethanol treatment in Example 1, was gradually admixed with the whipping cream with stirring. The admixed anhydrous crystalline β-maltose was completely dissolved in the whipping cream, and after a brief interval, hydrous crystalline β-maltose was quickly crystallized from the cream and the whole content was solidified into a block form. The product is a solid whipping cream with a smooth texture and can be advantageously used for producing confectioneries.

Example 8

Anhydrous Crystalline β-Maltose as a Base for Powderizing Aqueous Solution

In order to investigate the effect of the anhydrous crystalline β-maltose converted by the ethanol treatment as a base for powderizing moisture-containing compositions, a powderizing test was carried out using deionized water as a model of moisture-containing compositions as follows. Ten grams of the anhydrous crystalline β-maltose converted by the ethanol treatment, obtained by the method in Example 1, was placed in a 200-ml glass beaker, and then 0.25 ml per once of deionized water was admixed with the crystal with stirring using a spoon. The usefulness of the crystal was judged by the amount of deionized water added to the limit of keeping the powder form. The form of the powder was evaluated by the following four phases: (1) powder; (2) lump (it keeps a powder form while it comprises lumps); (3) cake; and (4) paste. As a control, the anhydrous crystalline α-maltose used in Example 2 was treated by the same procedure. The test was carried out in a room where the temperature was kept at 25° C. The results of the test and the form of each sample after admixing with 1.25 ml of deionized water are shown in Table 7 and FIG. 15, respectively.

TABLE 7

| Amount of admixed water (ml) | Moisture content (%, w/w) | Anhydrous crystalline β-maltose converted by the ethanol treatment (Present invention) | Anhydrous crystalline α-maltose (Control) |
| --- | --- | --- | --- |
| 0.25 | 2.4 | Powder form | Powder form |
| 0.50 | 4.8 | Powder form | Powder form |
| 0.75 | 7.0 | Powder form | Lump form |
| 1.00 | 9.1 | Powder form | Cake form |
| 1.25 | 11.1 | Powder form | Paste form |
| 1.50 | 13.0 | Lump form | Not tested |
| 1.75 | 14.9 | Lump form | Not tested |
| 2.00 | 16.7 | Lump form | Not tested |

As is evident from the results in Table 7, the anhydrous crystalline β-maltose converted by the ethanol treatment kept its good powdery form when 1.25 ml or lower amount of deionized water was admixed (Symbol "a" in FIG. 15). When 1.5 to 2.0 ml of deionized water was admixed, it kept its powdery form even though it formed lumps. While, in the case of anhydrous crystalline α-maltose as a control, it kept its powdery form when 0.5 ml or lower amount of deionized water was admixed. However, it showed a lump form by 0.75 ml, cake form by 1.0 ml, and paste form by 1.25 ml of deionized water (Symbol "b" in FIG. 15). It can not keep its powdery form by admixing with 1.0 ml or higher amount of deionized water. The results indicate that the anhydrous crystalline β-maltose converted by the ethanol treatment is more useful than the anhydrous crystalline α-maltose, as a base for powderizing moisture-containing compositions.

Example 9

Anhydrous Crystalline β-Maltose as a Base for Powderizing Alcohols

Except for using dehydrated ethanol as a substitute of deionized water and admixing with 0.5 ml per once, the usefulness of the anhydrous crystalline β-maltose converted by the ethanol treatment as a base for powderizing alcohols was investigated by the same procedure as in Example 8. The results of the test and the form of each sample after admixing with 6 ml of dehydrated ethanol are shown in Table 8 and FIG. 16, respectively.

TABLE 8

| Amount of admixed ethanol (ml) | Ethanol Conc. (v/w %) | Anhydrous crystalline β-maltose converted by the ethanol treatment (Present invention) | Anhydrous crystalline α-maltose (Control) |
| --- | --- | --- | --- |
| 3.0 | 24.3 | Powder form | Powder form |
| 3.5 | 27.5 | Powder form | Lump form |
| 4.0 | 30.5 | Powder form | Cake form |
| 4.5 | 33.3 | Powder form | Cake form |
| 5.0 | 36.0 | Powder form | Cake form |
| 5.5 | 38.5 | Powder form | Paste form |
| 6.0 | 40.9 | Powder form | Paste form |
| 7.0 | 45.3 | Powder form | Not tested |
| 8.0 | 49.3 | Powder form | Not tested |
| 9.0 | 52.9 | Lump form | Not tested |
| 10.0 | 56.2 | Lump form | Not tested |
| 11.0 | 59.2 | Cake form | Not tested |

As is evident from the results in Table 8, the anhydrous crystalline β-maltose converted by the ethanol treatment kept its good powdery form when 8.0 ml or lower amount of dehydrated ethanol was admixed. When 9.0 to 10.0 ml of dehydrated ethanol was admixed, it kept its powdery form even though it formed lumps. While, in the case of anhydrous crystalline α-maltose as a control, it kept its powdery form when 3.0 ml or lower amount of dehydrated ethanol water was admixed. However, it showed a lump form by 3.5 ml, cake form by 4.0 to 5.0 ml, and paste form (see Symbol "b" in FIG. 16) by 5.5 ml or higher amount of dehydrated ethanol. It can not keep its powdery form by admixing with 4.0 ml or higher amount of dehydrated ethanol. The results indicate that the anhydrous crystalline β-maltose converted by the ethanol treatment is more useful than anhydrous crystalline α-maltose, as a base for powderizing alcohol-containing compositions.

Example 10

Powdery Brandy

One thousand grams of the powdery anhydrous crystalline β-maltose, converted by the ethanol treatment in Example 1, was put in a vessel, and then 300 ml of a commercially produced brandy (40% proof) was gradually admixed with the powder with stirring to make into a powdery brandy. The product is a moist powdery brandy and can be advantageously used for producing confectioneries.

INDUSTRIAL APPLICABILITY

The present invention provides a novel anhydrous crystalline β-maltose. The anhydrous crystalline β-maltose of the present invention has a relatively low moisture-absorbing property in comparison with conventional anhydrous crystalline β-maltose and can be easily handled as a powdery crystal. The anhydrous crystalline β-maltose of the present invention is quickly converted into hydrous crystalline β-maltose by absorbing moisture. In addition, since the anhydrous crystalline β-maltose of the present invention exerts advantageous effects in comparison with anhydrous crystalline α-maltose which has been used as a base for powderizing moisture-containing compositions, it can be advantageously used as a base for solidifying or powderizing moisture-containing or alcohol-containing compositions. Further, it is also expected that a porous crystal of the anhydrous crystalline β-maltose of the present invention can be used as not only maltose and a base for solidification or powderization but also as substances for stabilizing useful substances, microencapsulating volatile fragrances and whipping. The present invention, established the novel anhydrous crystalline β-maltose, the process for producing the same and uses, greatly contributes to various related fields such as sugar manufacturings, foods and beverages, cosmetics, and pharmaceuticals as well as scientific researches.

The invention claimed is:

1. An anhydrous crystalline β-maltose, which has a melting point of 154 to 159° C. and a β-anomer content of maltose of 90% or higher.

2. The anhydrous crystalline β-maltose of claim 1 which has characteristic peaks at diffraction angles (2θ) of 7.8°, 19.5°, 20.7°, and 22.6°, on a powdery X-ray diffraction diagram.

3. A process for producing the anhydrous crystalline β-maltose of claim 1, comprising:
    (a) suspending a hydrous crystalline β-maltose in ethanol; and
    (b) stirring and heating the resulting suspension at a temperature of 60° C. or higher for the dehydration.

4. A method of using the anhydrous crystalline β-maltose of claim 1, as a base for solidifying or powderizing moisture-containing or alcohol-containing composition, comprising:
(a) admixing the anhydrous crystalline β-maltose with a moisture-containing or alcohol-containing composition; and
(b) solidifying or powderizing the moisture-containing or alcohol-containing composition.

* * * * *